US00PP14010P29

(12) United States Plant Patent
Utecht

(10) Patent No.: US PP14,010 P2
(45) Date of Patent: Jul. 22, 2003

(54) GERANIUM PLANT NAMED 'FIP 165'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/259,749

(22) Filed: Sep. 30, 2002

(51) Int. Cl.[7] ..... A01H 5/00
(52) U.S. Cl. ..... Plt./332

(58) Field of Search ..... Plt./332

*Primary Examiner*—Kent Bell
(74) *Attorney, Agent, or Firm*—Foley & Lardner

(57) ABSTRACT

A new and distinct geranium plant named 'Fip 165' characterized by the combined features of deep purple double flowers, medium-green foliage with weak, rounded lobes and with distinct zonation, medium sized, moderately compact and bushy, trailing plant habit, and medium spring flowering response.

1 Drawing Sheet

Latin name of the genus and species of the plant claimed: *Pelargonium peltatum L'Héritier.*
Variety denomination: 'Fip 165'.

BACKGROUND OF THE INVENTION

The present invention comprises a new and distinct cultivar of geranium, botanically known as *Pelargonium peltatum,* and hereinafter referred to by the cultivar name 'Fip 165'.

'Fip 165' is a product of a planned breeding program which had the objective of creating new ivy geranium cultivars with deep red to deep violet flower color, double flower type, medium tall and well-branched plant habit.

'Fip 165' originated from a hybridization made by the inventor Angelika Utecht in a controlled breeding program in Galdar, Gran Canaria, Spain, in 1993.

The female parent was an unpatented hybrid seedling, no. 90-1072-1, having single-type, dark rose-red flowers and medium-green leaves with zonation. The male parent of 'Fip 165' was the patented variety 'Fisam' (U.S. Plant Pat. No. 8,327), characterized by light violet double flowers, distinctly zoned foliage, and medium tall plant habit.

'Fip 165' was selected as one flowering plant within the progeny of the stated cross by Angelika Utecht in 1994 in a controlled environment in Galdar, Gran Canaria, Spain. The first act of asexual reproduction of 'Fip 165' was accomplished when vegetative cuttings were taken from the initial selection in the fall of 1994 in a controlled environment in Galdar, Gran Canaria, Spain, by, or under the supervision of, Angelika Utecht.

Horticultural examination of plants grown from cuttings of the plant initiated in May 1999 in Hillscheid, Federal Republic of Germany, and continuing thereafter, has demonstrated that the combination of characteristics as herein disclosed for 'Fip 165' are firmly fixed and are retained through successive generations of asexual reproduction.

'Fip 165' has not been observed under all possible environmental conditions. The phenotype may vary significantly with variations in environment such as temperature, light intensity and day length.

The following observations, measurements, and comparisons describe plants grown in Hillscheid, Germany under greenhouse conditions which approximate those generally used in commercial practice.

BRIEF SUMMARY OF THE INVENTION

The following traits have been repeatedly observed and are determined to be basic characteristics of 'Fip 165' in combination distinguish this geranium as a new and distinct cultivar:

1. Relatively large, deep purple colored flowers, double flower form;
2. medium sized, semi-spherically shaped inflorescences;
3. medium-green leaves with very weak lobes and distinct zonation;
4. moderately compact, semi-trailing, but well-branched plant habit; and
5. medium (mid season) spring flowering response.

Of the many commercial cultivars known to the present inventor, the most similar in comparison to 'Fip 165' is the patented variety 'Fislulu' (U.S. Plant Pat. No. 12,228), and the unpatented commercial variety 'Tomcat'.

In comparison to 'Fislulu', 'Fip 165' has an even deeper and somewhat less bluish hue of flower color, mainly RHS 187C, in contrast to RHS 61 A to RHS 66 A for 'Fislulu'. Plant size of 'Fip 165' is typically somewhat taller than of that of 'Fislulu'.

In comparison to 'Tomcat', 'Fip 165' has a somewhat more bluish, less reddish tone of purple flower color, and plant habit is more bushy and uniform with somewhat shorter internodes.

BRIEF DESCRIPTION OF THE DRAWING

The accompanying photographic drawing shows typical flower and foliage characteristics of 'Fip 165' with colors being as true as possible with an illustration of this type. The drawing shows a branch end of a typical 'Fip 165' plant with leaves, buds and inflorescences.

DETAILED BOTANICAL DESCRIPTION

Measurements were taken in Hillscheid, Germany, in mid May 2002, about 15 weeks after planting of rooted cuttings. The plants were growing in 14 cm plastic pots and had been pinched once. In the following description color references are made to The Royal Horticultural Society Colour Chart. The color values were determined indoors from plants developed in a green-house, as described.

Inflorescence:
- *Type.*—Umbel, roughly semi-spherically shaped.
- *Average diameter.*—108 mm.
- *Average depths.*—71 mm.
- *Peduncle length.*—135 mm.
- *Peduncle color.*—Green, RHS 143 B.
- *Pedicel.*—28 mm long, with spur.
- *Pedicel color.*—Mainly green, RHS 143 B, in parts brown, RHS 181 A.
- *Number of flowers per umbel.*—About 9–11.

Corolla:
- *Average diameter.*—55 mm.
- *Form.*—Double-type.
- *Shape.*—Outer petals form an almost flat ring with round outline, inner petals at a right angle and somewhat irregularly arranged in the middle of the corolla.
- *Number of petals.*—12–15.
- *Number of petaloids.*—2–3 (same color as petals).
- *Shape of petals.*—Obovate, base acute, upper end truncate or rounded, margin entire, surface velvety.
- *Size of petals.*—Upper petals: 30 mm long, 18–20 mm wide. lower petals: 23–25 mm long, 16–18 mm wide.
- *Color (general tonality from a distance of three meters)* .—Deep purple, with a blackish overtone.
- *Color of upper petals.*—Main part RHS 187 C, in parts with a blackish overtone, RHS 187 A.
- *Markings of upper petals.*—Two blackish veins, RHS 187 A, relatively strong, also visible on the underside.
- *Color of lower petals.*—RHS187 C.
- *Markings of lower petals.*—None.
- *Color of lower surface of petals.*—Between RHS 61 A and RHS 74 A, marbled, occasionally lighter margins RHS 70 C.
- *Color of sepals.*—Outer surface: light green, RHS 143 C, largest sepal weakly brownish RHS 181 C; inner surface: light green, RHS 143 C, largest sepal weakly brownish infused, RHS 181 C.
- *Number of sepals.*—5.
- *Shape of sepals.*—Linear to lanceolate, acute tip, truncate base, surface with moderate pubescence, margin entire.
- *Size of sepals.*—12–14 mm long, 5 mm wide for the largest upper sepal, 3 mm in width for the other sepals.

Bud (just prior to petals unfolding):
- *Shape.*—Elliptical, surface sparsely covered with hair.
- *Color of sepals.*—Light green, RHS 143 C.
- *Color of petals.*—RHS 78 A.
- *Length.*—24 mm.
- *Width.*—10 mm.

Reproductive organs:
- *Androecium.*—2–5 fertile anthers, plenty pollen, yellow-orange, RHS 28 A, lower side of anthers blackish, RHS 187 A, filaments mainly white, RHS 155 D, to light-pink, RHS 68 B.
- *Gynoecium.*—One pistil, whitish style, RHS 155 D to 65 D, stigma 5–6-lobed, dark-purple, RHS 187 B.
- *Fertility/seed set.*—No seed set observed.

Spring flowering response period: In Hillscheid, Germany, in 2002 plants (pinched plants) had on average 0.4 flowers opened 15 weeks after planting of rooted cuttings.

Outdoor flower production: Continuously and moderately rich flowering the flower count in 2002 in Hillscheid, Germany, indicated about 4–5 inflorescence per plant in mid May.

Durability: Good shatter resistance, fair rain resistance, and relatively good stability of flower color, hardly fading.

Lastingness of the individual flower: About 8–9 days at 18° C.

Fragrance: None.

PLANT

Foliage:
- *Shape.*—Ivy-shaped, with cordate base, with the gap between the lowest lobes mostly closed, respective with the margins of the lowest lobes overlapping, apex rounded with relatively weak lobes.
- *Margin.*—Entire.
- *Texture.*—Leathery, upper surface smooth, glossy.
- *Size of leaf.*—82 mm wide, 48 mm long.
- *Color of upper surface.*—Medium green, between 137 D and 143 A.
- *Color of zonation.*—Brown ring in the middle of the leaf, color about RHS 166 A, distinctness weak to medium.
- *Color of lower surface.*—RHS 143 C.
- *Petioles.*—Mostly 35–45 mm long, approximately 3 mm diameter, light green in color, RHS 143 C.

General appearance and form:
- *Stem color.*—Medium to light green, RHS 143 A to 143 B.
- *Internode length.*—35–45 mm.
- *Branching pattern.*—7.2 branches.
- *Length of plants.*—23 .0 cm (15-week-old plants, as described) 70–75 cm (about 28-week-old plants in mid August) as measured from the top of the soil (base of the main stem) to the tips of the branches without inflorescences.

Pest/disease resistance/susceptibility: No observations to date.

I claim:

1. A new and distinct cultivar of geranium plant named 'Fip 165', as described and illustrated herein.

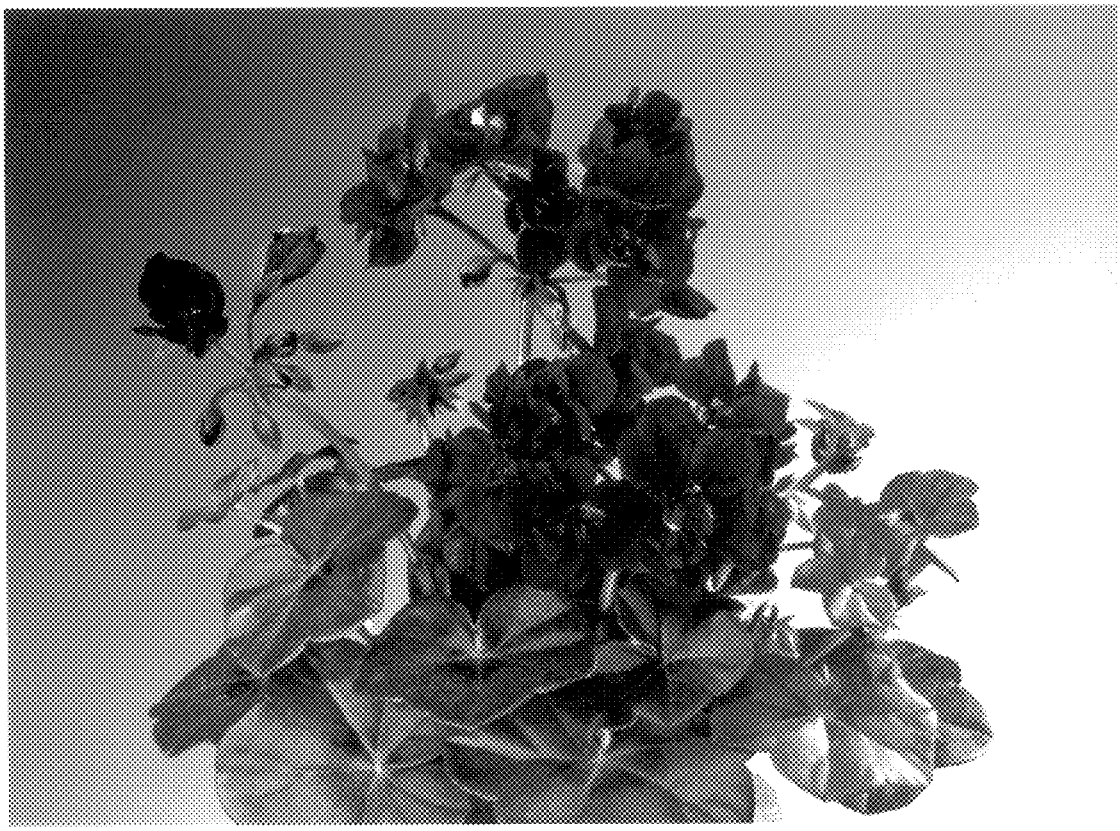

* * * * *